US00RE49865E

(19) United States
(12) Reissued Patent
Docken et al.

(10) Patent Number: US RE49,865 E
(45) Date of Reissued Patent: Mar. 5, 2024

(54) RECONCILIATION OF DATA ACROSS DISTINCT FEATURE SETS

(71) Applicant: IQVIA Inc., Parsippany, NJ (US)

(72) Inventors: Jeremy Grant Docken, Chicago, IL (US); David Shoichi Chan, Los Angeles, CA (US)

(73) Assignee: IQVIA Inc., Parsippany, NJ (US)

(21) Appl. No.: 17/480,921

(22) Filed: Sep. 21, 2021

Related U.S. Patent Documents

Reissue of:
(64) Patent No.: 10,423,761
Issued: Sep. 24, 2019
Appl. No.: 14/807,144
Filed: Jul. 23, 2015

U.S. Applications:
(60) Provisional application No. 62/139,534, filed on Mar. 27, 2015.

(51) Int. Cl.
*G16H 20/10* (2018.01)
*G16H 20/13* (2018.01)
*G16H 40/67* (2018.01)

(52) U.S. Cl.
CPC ..... *G16H 20/10* (2018.01); *G16H 20/13* (2018.01); *G16H 40/67* (2018.01)

(58) Field of Classification Search
CPC ..... G16H 20/13; G16H 20/10; G16H 40/67
See application file for complete search history.

(56) References Cited

U.S. PATENT DOCUMENTS

2008/0222042 A1* 9/2008 Moore ..... G06F 19/3456 705/55
2010/0131284 A1* 5/2010 Duffy ..... G06Q 30/02 705/2
2015/0006261 A1* 1/2015 Gutman ..... G06F 3/0482 705/7.39

OTHER PUBLICATIONS

Dean, J. Michael, "Probabilistic Linkage of Computerized Ambulance and Inpatient Hospital Discharge Records: A Potential Tool for Evaluation of Emergency Medical Services," Annals of Emergency Medicine 37:6. dated Jun. 2001, pp. 616-626.

Dean, J. Michael. Probabilistic Linkage of Computerized Ambulance and Inpatient Hospital Discharge Records: A Potential Tool for Evaluation of Emergency Medical Services. Jun. 2001. Annals of Emergency Medicine 37:6. pp. 616-626. (Year: 2001).*

(Continued)

*Primary Examiner* — Jalatee Worjloh
(74) *Attorney, Agent, or Firm* — Fish & Richardson P.C.

(57) ABSTRACT

Methods, systems, and apparatus, including computer programs encoded on a computer storage medium, for linking a first electronic data set to a second set of data fields in a second electronic data set. Automatically identifying a prescribing physician identifier based on the linked first and second electronic data sets. Determining a relationship between a physician associated with the prescribing physician identifier and at least one of the approved entities based on comparing the prescribing physician identifier and identifiers of the one or more approved entities to a fourth set of data fields from a fourth electronic data set. Automatically generating an electronic notification indicating that a product sold by the merchant is eligible for the discount in response to determining a relationship between a physician and the at least one of the approved entities.

44 Claims, 5 Drawing Sheets

(56) References Cited

OTHER PUBLICATIONS

Lewis, Jeffrey, "The Future of the 340B Drug Pricing Program: Challenges and Opportunities," www.sentryds.com/wp-content/uploads/wp-thefutureofthe340Bdrugpricingprogram.pdf., Oct. 2011, 18 pages.
Public Law 102-585, Section 340B, "Public Health Service Act," The Veterans Health Care Act of 1992, dated Nov. 4, 1992, 8 pages.

* cited by examiner

RECONCILIATION OF DATA ACROSS DISTINCT FEATURE SETS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application *is a reissue application of U.S. patent application Ser. No. 14/807,144, filed Jul. 23, 2015, now issued U.S. Pat. No. 10,423,761, issued Sep. 24, 2019, which* claims the benefit of U.S. Provisional Patent Application No. 62/139,534, filed Mar. 27, 2015, the entirety of which is hereby incorporated by reference as if fully set forth therein.

BACKGROUND

Pharmaceutical manufacturers that wish to have their products reimbursed by Medicaid or Medicare must agree to provide certain statutorily-defined entities ("340B certified entities") with higher-than-normal discounts. Some manufacturers also provide significant non-340B discounts but exclude drugs acquired under the 340B program from being eligible to receive a non-340B rebate (called a "duplicate discount"). Currently, manufacturers are only able to identify potential duplicate discounts based on identifying if the dispensing entity is a 340B eligible entity. However, retail pharmacies may contract with 340B certified entities to dispense 340B-acquired drugs on behalf of the covered entity. Because health care data related to prescriptions, product sales, and approved associations between pharmacies and certified entities are stored in electronic data sources across disparate unrelated datasets with distinct feature sets, manufacturers have little ability to differentiate when a retail pharmacy is dispensing a 340B product from when the retail pharmacy is dispensing a product acquired at a normal commercial price.

SUMMARY

In general, innovative aspects of the subject matter described in this specification can be embodied in methods that include actions of receiving a first electronic data set, including a first set of data fields from a first party, where the first electronic data set includes prescription fulfillment data. Linking the first electronic data set to a second set of data fields in a second electronic data set, where the linking is based on matching data from at least one the first set of data fields of the first electronic data set to data from at least one of a second set of data fields of the second electronic data set. The second electronic data set includes third-party prescription information. Automatically identifying a prescribing physician identifier based on the linked first and second electronic data sets. Accessing a third electronic data set, where the third electronic data set includes discount eligibility information and identifies entities approved to receive a discount. Automatically identifying within the accessed third electronic data set one or more approved entities having an approved relationship with a merchant, based on a merchant identifier from one of the data fields in the first data set of data fields, where the merchant is associated with the merchant identifier. Determining a relationship between a physician associated with the prescribing physician identifier and at least one of the approved entities based on comparing the prescribing physician identifier and identifiers of the one or more approved entities to a fourth set of data fields from a fourth electronic data set. Automatically generating an electronic notification indicating that a product sold by the merchant is eligible for the discount in response to determining the relationship between the physician and the at least one of the approved entities. Other implementations of this aspect include corresponding systems, apparatus, and computer programs, configured to perform the actions of the methods, encoded on computer storage devices.

These and other implementations can each optionally include one or more of the following features. The operations may include reconciling data from the first, second, third, and fourth data sets with data from a fifth electronic data set to determine information related to a sale of the product, and the notification may include the information related to the sale of the product. Determining the relationship between a physician associated with the prescribing physician identifier and at least one of the approved entities can include determining, from data in the fourth set of data fields, that the relationship existed on a dispense date of the product, where the dispense date is included in data from the first set of data fields. The operations may include determining, from data in the third electronic data set, that the approved relationship between the merchant and at least one of the approved entities with which the physician has a merchant relationship existed on a dispense date of the product, where the dispense date is included in data from the first set of data fields.

The alert may include a confidence score indicating a likelihood that the product is eligible for the discount. The confidence score may be determined based on a type of the relationship between the physician and the at least one of the approved entities. The confidence score may be determined based on a number of relationships that the physician has with approved entities.

The second electronic data set may be a secure data set, the method further comprising accessing the second electronic data set from a secure data repository. The discount may be a government mandated discount and wherein the third electronic data set is a government maintained data set.

Particular implementations of the subject matter described in this specification can be implemented so as to realize one or more of the following advantages. Implementations may provide a uniquely linked database of distinct features from across multiple disparate data sources that permits accurate tracking of complex electronic transactions. Implementations may improve the tracking of 340B discount eligible product sales. Implementations may provide a reliable system for tracking "duplicate discounts" on pharmaceutical products.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Implementations of the present disclosure relates generally to reconciling data from multiple electronic data sources across disparate datasets having distinct feature sets. More specifically, implementations of the present disclosure are related to reconciling health care data from multiple different data sources such as, for example, product sales data, insurance data, prescription data, and government agency data to determine the eligibility status of pharmaceutical products for government mandated discounts. Implementations of the present disclosure include reconciling and linking the specific data features from across multiple data sets into a uniquely linked database that permits a user to accurately track complex transactions. For example, computing systems using the reconciled electronic data sets can provide pharmaceutical manufacturers with actionable information indicating whether particular product sales are eligible for government mandated discounts.

Moreover, while advances in computer technology have greatly increased the amount of available information, the sheer volume of information can be overwhelming and cumbersome to the extent that processors may struggle to operate on datasets in time such that a user receives actionable information. Therefore, by reconciling the disparate datasets into a uniquely linked database, the user is provided with an investigative tool that allows the retrieval of actionable information that would not otherwise be available.

Implementations of the present disclosure will be discussed in further detail with reference to an example context. The example context includes a health care data services environment. It is appreciated, however, that implementations of the present disclosure can be realized in other appropriate contexts, for example, consumer data services, financial data services, government or political data services, marketing data services, public opinion data services, etc.

Figure 1:
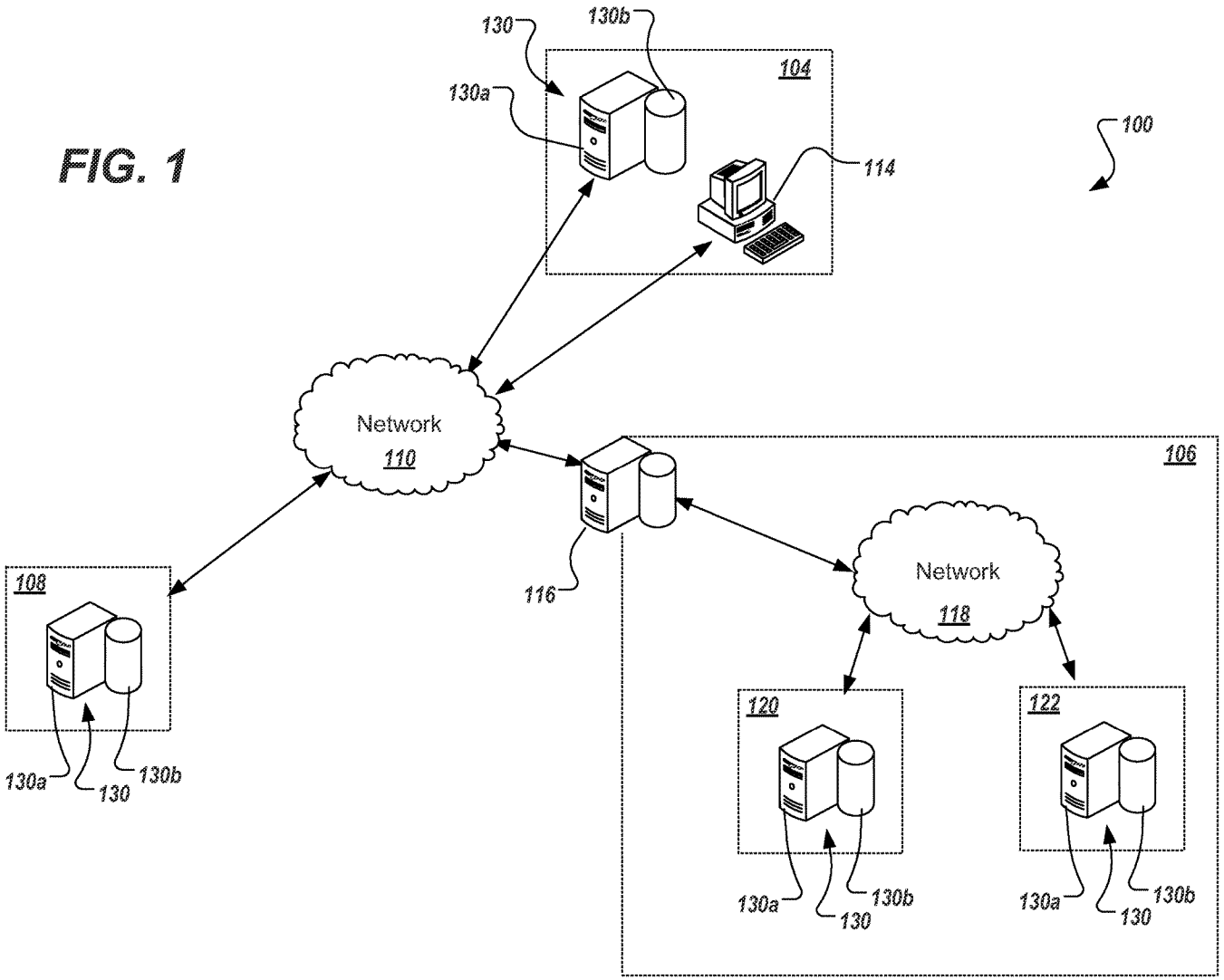
FIG. 1 depicts an example system in accordance with implementations of the present disclosure.

FIG. 1 depicts an example system 100 that can execute implementations of the present disclosure. The example system 100 is illustrated in a health care data services environment, including a client organization 104, an information services organization (ISO) 106, and one or more external systems 108. The ISO 106 may be a business, non-profit organization, or government entity that provides information services to other organizations or individuals. Client organization 104 may be, for example a pharmaceutical manufacturer, a hospital, a pharmacy, a health insurance entity, or a pharmaceutical benefit manager (PBM). The external systems 108 may be, for example, third-party data providers such as government agency data systems.

Each of the client organization 104, the ISO 106, and the external systems 108 include one or more computing systems 130. The computing systems 130 can each include a computing device 130a and computer-readable memory provided as a persistent storage device 130b, and can represent various forms of server systems including, but not limited to a web server, an application server, a proxy server, a network server, or a server farm. In addition, each of the client organization 104, the ISO 106, and the external systems 108 can include one or more user computing devices 114. However, for simplicity, a user computing device 114 is only depicted at the client organization 104. Computing devices 114 may include, but are not limited to, one or more desktop computers, laptop computers, notebook computers, tablet computers, and other appropriate devices.

In addition, the ISO 106 can include, for example, one or more data reconciliation systems (DRS) 116. A DRS 116 can be one or more computing systems 130 configured to perform data reconciliation between distinct electronic data sets distributed across multiple separate computing systems in accordance with implementations of the present disclosure. The ISO 106 also includes one or more data repository systems 120,122. In some examples, the data repository systems 120,122 include one or more databases storing data compiled by the ISO 116. In some implementations, one or more of the data repository systems 120,122 can be a secure data repository storing sensitive data in one or more secure data sets. For example, a secure data repository can be a data repository with restricted access and may require special credentials to obtain access. For example, a secure data repository may contain confidential information, personally identifiable information or other protected information. Furthermore, the data in the secure data repository can be encrypted.

The DRS 116 at the ISO 106 communicates with computing systems 130 at the client organization 104 and the external systems 108 over network 110. The network 110 can include a large network or combination of networks, such as a PSTN, a local area network (LAN), wide area network (WAN), the Internet, a cellular network, a satellite network, one or more wireless access points, or a combination thereof connecting any number of mobile clients, fixed clients, and servers. In some examples, the network 110 can be referred to as an upper-level network. In some examples, ISO 106 may include, for example, an internal network (e.g., an ISO network 118). The DRS 116 can communicate with the computing systems 130 of the one or more of the data repository systems 120,122 over the ISO network 118.

Figure 2:
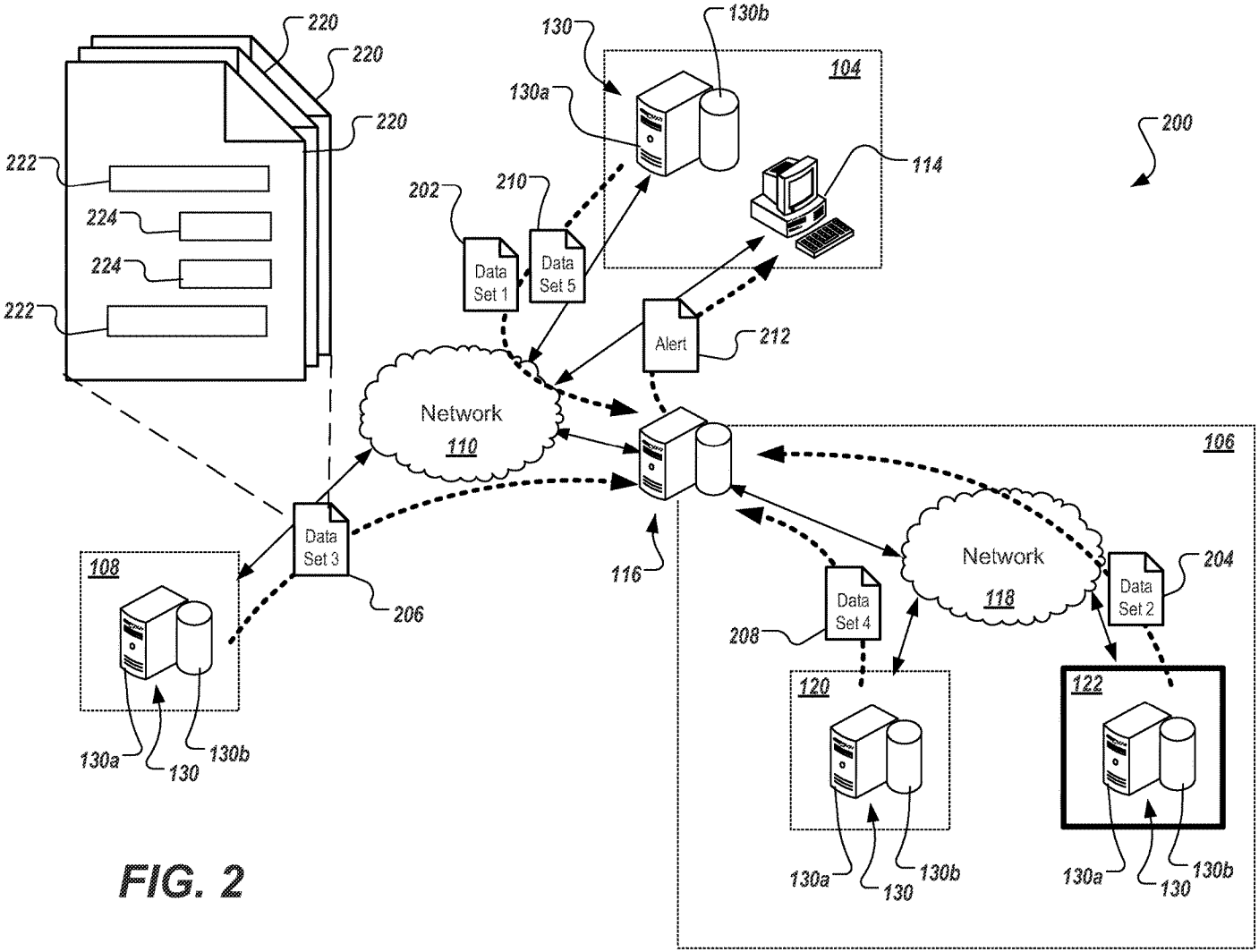
FIG. 2 depicts an example data reconciliation process flow within the example system.

FIG. 2 depicts an example data reconciliation process flow 200 within the example system 100. The process flow 200 involves reconciliation of data between distinct electronic data sets distributed across multiple separate computing systems, and can be performed by the DRS 116. In the example healthcare data services context, the DRS 116 can reconcile the data contained in the data sets to automatically determine whether a pharmaceutical product sold by a merchant was eligible for a manufacturer discount by verifying whether a prescribing physician has an association with an approved entity. An approved entity can be an entity that was certified to receive a discount on pharmaceutical products at the time the physician issued the prescription. Furthermore, in response to making such a determination, the DRS 116 can send an electronic notification (e.g., alert 112) including supporting data from the appropriate data sets to the client organization 104.

For example, the DRS 116 accesses at least a portion of data from each of several electronic data sets (e.g., electronic data sets 202, 204, 206, 208, 210). For example, a client organization 104 can transmit all or part (e.g., less than all of the data records 220) of a data set (e.g., data set 1 or data set 5) to the DRS 116. In some examples, the DRS 116 can obtain remote access to a data set (e.g., data set 3) from an external system 108 to search the data records of the data set.

Each of the electronic data sets can include a plurality of data records 220. Data can be organized into a plurality of data fields 222 and sub-fields 224 within each record 220. In some examples, each data set has distinct features, data fields, data formats and other distinct properties. In some examples, each electronic data set can include between millions, tens of millions, or hundreds of millions of data records 220. In some examples, the data records and/or the data contained in the data fields can be encrypted.

The DRS 116 reconciles data across the data sets by analyzing data in each data set, identifying corresponding data fields in other data sets, and searching the records of the other data sets to find matching data in the corresponding data fields to identify one or more corresponding data records. The DRS 116 can extract data from distinct data fields of the other data sets (e.g., data fields including data not present one or more of the analyzed data sets). The DRS 116 can use the extracted data to further reconcile the data sets. In some examples, the DRS 116 can analyze the extracted data to automatically generate a reconciliation report in the form of an electronic notification 212. In some examples, the data reconciliation process flow can be an interactive process.

Figure 3:
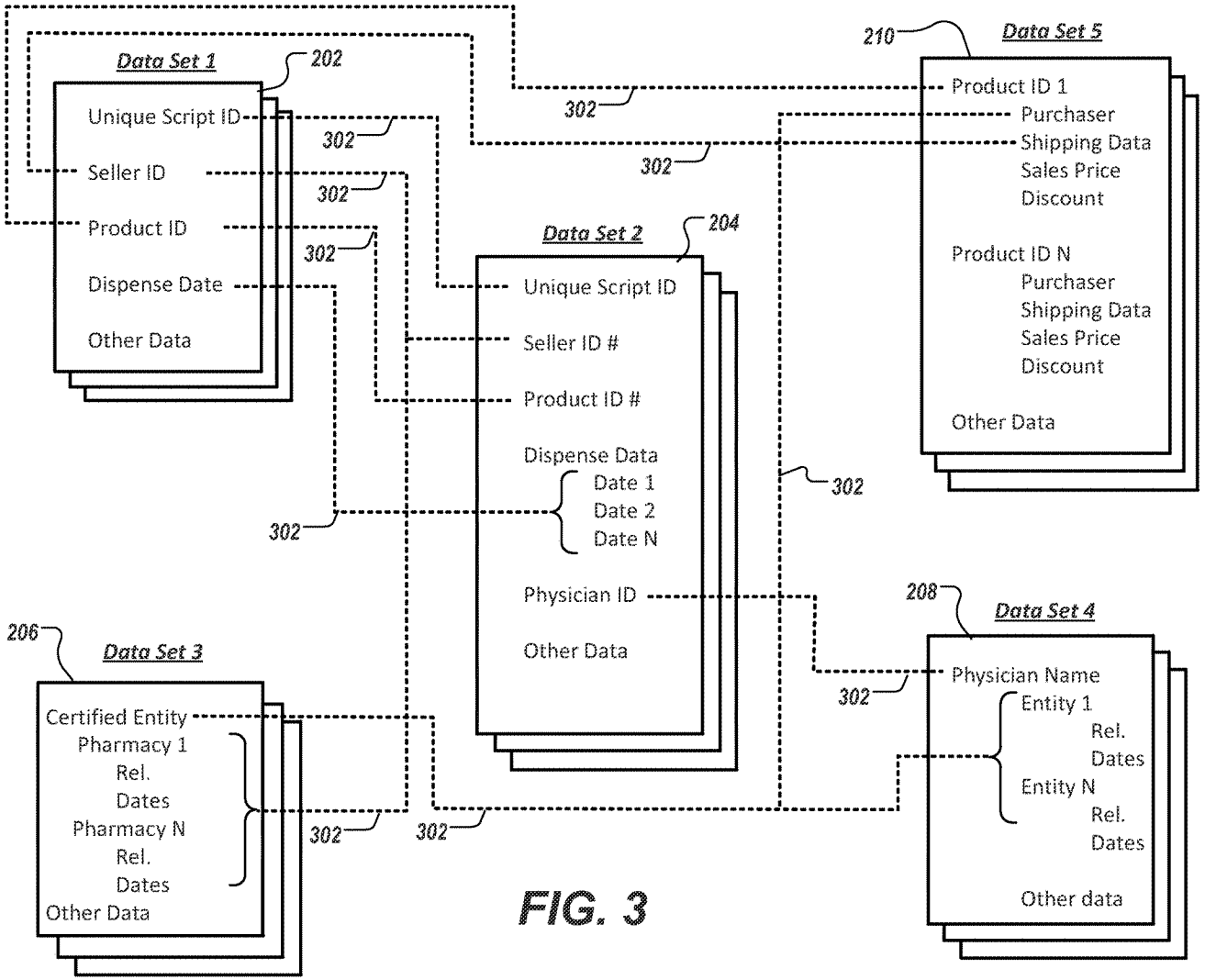
FIG. 3 depicts example data sets in accordance with implementations of the present disclosure.

The data reconciliation process flow 200 is described in more detail in reference to FIGS. 2 and 3. FIG. 3 depicts example data sets in accordance with implementations of the present disclosure and provides a graphical representation of the example data reconciliation process flow of FIG. 2. For example, in the example health care data services context, data set 1 (202) includes prescription fulfillment data, data set 2 (204) includes third-party prescription information compiled by, for example, the ISO 106, data set 3 (206) includes discount eligibility information, data set 4 (208) includes a directory of physicians, and data set 5 (210) includes product sales data. Edges 302 represent relationships established by the DRS 116 between data contained in the various data sets. Electronic data set 1 (202) includes data contained in data fields such as, for example, Unique Script ID, Seller ID, Product ID, Dispense Date, in addition to other data fields. Electronic data set 1 (202) includes data contained in data fields such as, for example, Unique Script ID, Seller ID, Product ID, and Dispense Date, in addition to other data fields. Electronic data set 2 (204) includes data contained in data fields such as, for example, Unique Script ID, Seller ID, Product ID, Dispense Dates (e.g., Dates 1-N), and Physician ID, in addition to other data fields. Electronic data set 3 (206) includes data contained in data fields such as, for example, Certified Entity in addition to other data fields, and sub-fields including Merchant ID sub-fields 1-N and Relationship and Date sub-fields indicating a relationship and dates of the relationship between the Certified Entity and each Merchant identified by the Merchant ID sub-fields. Electronic data set 4 (208) includes data contained in data fields such as, for example, Physician ID and Entities 1-N in addition to other data fields, and sub-fields including Relationship and Date sub-fields indicating a relationship and dates of the relationship between a physician and each entity identified by the Entity fields. Electronic data set 5 (210) includes data contained in data fields such as, for example, Product ID, Purchaser, Shipping Data, Sales Price, and Discount, in addition to other data fields.

Continuing the description of the example data reconciliation process flow 200 in reference to FIGS. 2 and 3, the DRS 116 receives electronic data set 1 (202) from the client organization 104. In addition, the DRS 116 accesses electronic data set 2 (204), for example, from data repository system 122. The DRS 116 can analyze and extract appropriate data from one or more of data set 1's data fields, and use the extracted data to search for corresponding records in data set 2 (204) to automatically identify additional information related to the data in data set 1. For example, data set 1 (202) may include information related to a prescription and pharmaceuticals sold under the prescription, but not include a prescribing physician. The DRS 116 can automatically identify and use the information from data set 1 to locate corresponding records in data set 2. The DRS 116 can then identify information from the records of data set 2 that identifies the prescribing physician who wrote the prescription identified by the information in data set 1. For example, the DRS 116 can search corresponding data fields of data set 2 for matching data from the data set 1. In some examples, the DRS 116 can link data set 1 and data set 2 (or records from data set 1 and data set 2) based on matching data contained in the two data sets. As illustrated in FIG. 3 data from the Unique Script ID, Seller ID, and Product ID fields form data set 1 (202) are matched with data in corresponding data fields of data set 2 (204).

For example, data set 1 (202) may identify a prescription using a unique prescription identification code (e.g., Script ID or RxID), and can include an identity (e.g., name or identification code) for the product sold under the prescription (e.g., a pharmaceutical product such as a prescription drug identified in the Product ID field), an identity (e.g., name and address or identification code of a specific pharmacy or chain of pharmacies in the Seller ID field) of a merchant that sold the product, and the date that the product was sold (e.g., Dispense Date). Similarly data set 2 (202) may identify the same prescription and include additional information such as, for example, an identity (e.g., a name and address or identification code in the Physician ID field) of a physician that wrote the prescription a list of multiple dates on which the prescription was fulfilled (e.g., for a prescription that requires regular refills). The DRS 116 can automatically identify the prescribing physician's identifier from data set 2 (204) based on the data sets 1 and 2.

In addition, the DRS 116 accesses electronic data set 3 (206) from an external system 108. Using the data from the Seller ID field of data set 1, the DRS 116 can automatically identify one or more records from data set 3 (206) associated with a merchant identified in the Seller ID field of data set 1, for example, a pharmacy that sold a pharmaceutical product identified in data set 1 (202). In addition, data set 3 (206) contains data related to certified entities (e.g., an entity approved to receive a discount on a pharmaceutical product) such as, for example, merchants having approved associations with the certified entity (e.g., Merchant ID fields), a status of the association (e.g., Relationship fields), and effective dates of the relationships (e.g., Date fields). For example, from data set 3 (206), the DRS 116 can verify whether the merchant had an approved relationship with one or more certified entities on the date that the pharmaceutical product from data set 1 (202) was dispensed.

The DRS 116 can use the identities of the one or more certified entities from data set 3 (206) and the physician ID form data set 2 (204) to determine whether the physician was associated with any of the same certified entities with which the merchant also has an approved relationship from data set 4 (208). In addition, the DRS 116 can determine an association type for associations that the physician may have with any of the same certified entities. For example, the DRS 116 can access electronic data set 4 (208) from data repository system 120, and data set 4 (208) may include physician directory information including which entities (e.g., hospitals and clinics) the physicians have associations with (e.g., Entity fields), the types of relationships (e.g., Relationship fields), and the effective dates of the relationships (e.g., Date fields). The DRS 116 can identify a data record in data set 4 (208) related to the physician from data set 2 (204), and compare the certified entities identified from data set 3 (206) with the entities with which that the physician is associated in the identified data set 4 (208) record. In other words, the DRS 116 can use data from data sets 2, 3 and 4 to determine whether the physician has (or had) an association with any of the same certified entities as the merchant that sold a pharmaceutical product identified by data set 1 (202), the type of association the physician has with the certified entity, and the effective dates of the association. In some examples, the DRS 116 will verify whether the physician had an association with the certified entity on or near the date that the pharmaceutical product from data set 1 was sold (e.g., date dispensed from data set 1), and the type of the association. For example, association types may include attending, IDN affiliated, admitting, or staff. In addition, the DRS 116 can use data in data set 4 to identify other entities with which the physician has associations, the number of other associations, the type of those associations, and their effective dates (e.g., when the associations began and if or when the associations changed or ended).

In response to determining that the physician has an association with any of the same certified entities as the merchant that sold a pharmaceutical product identified by data set 1 (202), the DRS 116 automatically generates and sends an electronic notification to the client organization (e.g., user computing device 114) indicating that a product sold by the merchant may be eligible for a discount. The electronic notification (e.g., alert 212) can be an e-mail, text message, etc. In some examples, the notification includes applicable data from one or more of the data sets to document the determination made by the DRS 116.

Thus, by reconciling the data contained in data sets 1, 2, 3, and 4, the DRS 116 can automatically determine whether a pharmaceutical product sold by a merchant was eligible for a manufacturer discount. More specifically, the data contained in data sets 1, 2, 3, and 4, the DRS 116 can verify whether a prescribing physician had an association with an entity certified to receive a discount on pharmaceutical products at the time the physician issued the prescription. Furthermore, in response to making such a determination, the DRS 116 can sent an electronic notification including supporting data from the appropriate data sets to the client organization 104.

Figure 4:
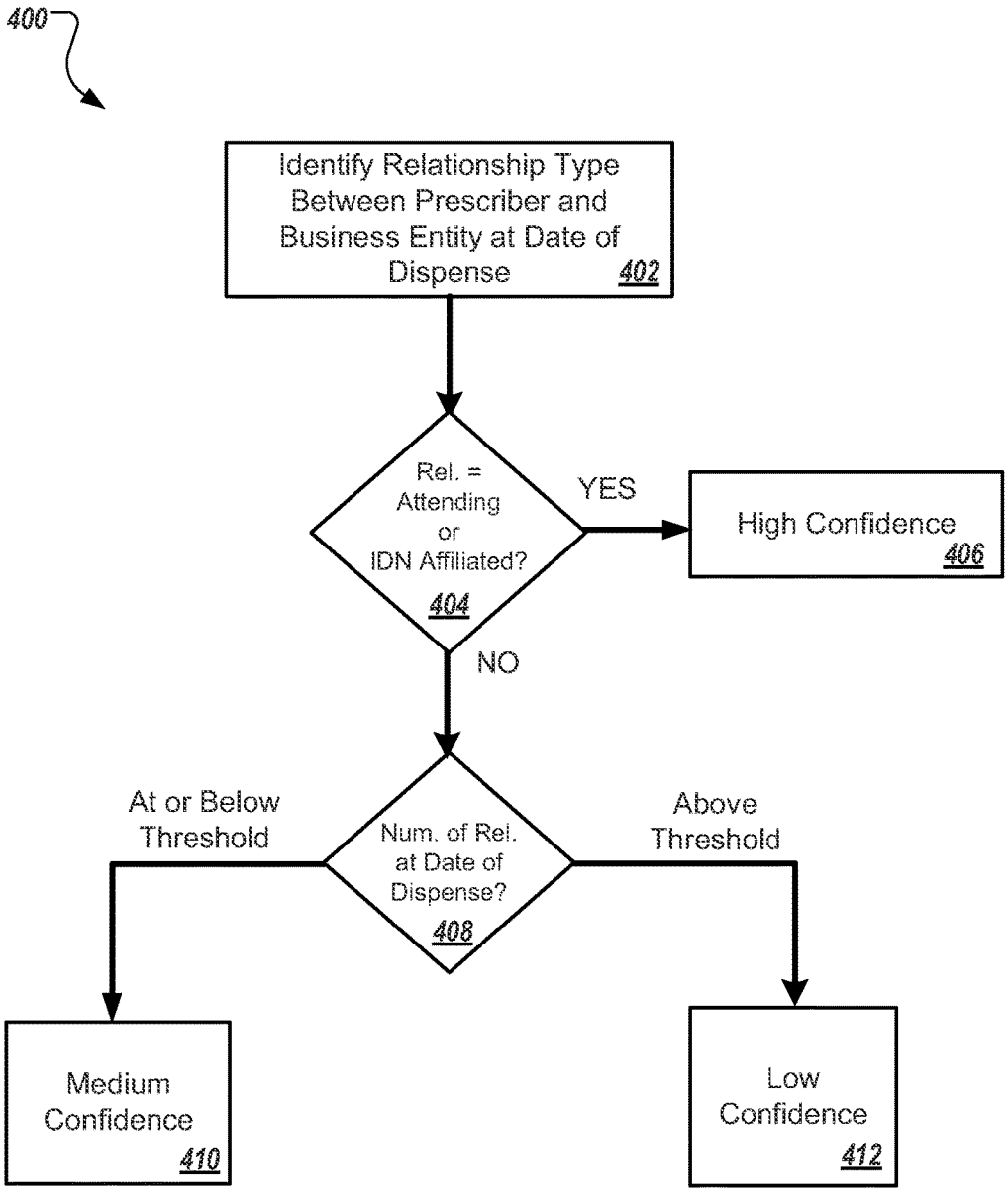
FIG. 4 depicts an example process for determining reconciliation confidence that can be executed in accordance with implementations of the present disclosure.

In some examples, the DRS 116 can use the physician data obtained from data set 4 (208) to determine a confidence level associated with data contained in the electronic notification, as illustrated in FIG. 4. The confidence level can indicate a likelihood that the pharmaceutical product sold by the merchant under the prescription identified from data set 1 (202) was eligible for a manufacturer discount. FIG. 4 depicts an example process 400 for determining reconciliation confidence that can be executed in accordance with implementations of the present disclosure. In some examples, the example process 400 can be provided as one or more computer-executable programs executed using one or more computing devices such as, for example, DRS 116.

Referring to FIGS. 2-4, upon determining that the physician has an association with any of the same certified entities as the merchant that sold a pharmaceutical product identified by data set 1 (202), the DRS 116 identifies the type relationship(s) that the prescribing physician has or had with the certified entities at the date that the pharmaceutical product was prescribed (402). Types of association relationship(s) may include, for example, attending, IDN affiliated, admitting, or staff. If the identified physician has either an attending or IDN affiliated relationship with one of the certified entities (404) the confidence level is set to a high confidence level (406). For example, attending and IDN affiliated relationships may indicate a high likelihood that the physician was working under his/her association with the certified entity when the identified prescription for the pharmaceutical product was issued.

Otherwise, if the physician does not have an attending or IDN affiliated relationship with one of the certified entities (404), the DRS 116 determines the number of associations that the physician has or had with certified entities at the date that the pharmaceutical product was prescribed (408). If the number of certified entities with which the physician has an association is at or below a threshold number then the confidence level is set to a medium confidence level (410). Conversely, if the number of certified entities with which the position has an association is above a threshold number then the confidence level is set to a low confidence level (412).

For example, if the prescribing physician has admitting or staff relationships with multiple different entities, some of which are certified entities and some of which are not certified entities, there is a moderate likelihood that the pharmaceutical product was prescribed in connection with the physician's association with one of the certified entities. Even more, if some of the certified entities with which the physician is associated are not also associated with the merchant that sold a pharmaceutical product identified by data set 1 (202), there is a lesser likelihood the pharmaceutical product was sold in relation to one of the certified entities.

In some implementations, the number of associations that the physician has may be represented by a ratio. For example, the number of associations may be represented by a ratio as the number of associations that the physician has with certified entities to the total number of associations that the physician has with both certified and noncertified entities. In some examples, the ratio may be one of the number of associations that the physician has with certified entities in common with the merchant that sold the pharmaceutical product to the total number of associations that the physician has with both certified and noncertified entities.

Referring again to FIGS. 2 and 3, in some examples, the DRS 116 also reconciles data from data set 5 (210) with related data from data sets 1, 3, and 4 to establish information related to a sale of the pharmaceutical product. Electronic data set 5 (210) includes information related to the sale of pharmaceutical products such as, for example, product identification data (e.g., product codes), purchaser data (e.g., an identity of and payment information form a purchaser), shipping data (e.g., recipient identity and address), regular sales price, and any discounts applied to the sale. The DRS 116 can determine whether any sales data from data set 5 identifies a pharmaceutical product purchased by the certified entity and sent to the merchant that filled the physician's prescription, and thereby, further verify both whether and which discounts have already been applied to the pharmaceutical product. In addition, the notification can include appropriate sales data identified from data set 5 (210).

In some examples, data set 1 can include prescription fulfillment data from a Pharmacy Benefits Manager (PBM). In some examples, data set 3 can include discount eligibility information related to entities entitled to receive a government mandated discount under a government program such as, for example, the 340B drug discount program.

In some implementations, the second and first data sets (e.g., 202 and 204) may be combined into a single data set. For example, Medicaid prescriptions data may be included in one data set that contains the feature sets similar to those of both example data set 1 (202) and data set 2 (204). In such implementations, steps related to linking data from example data set 1 (202) and data set 2 (204) would not be necessary.

Figure 5:
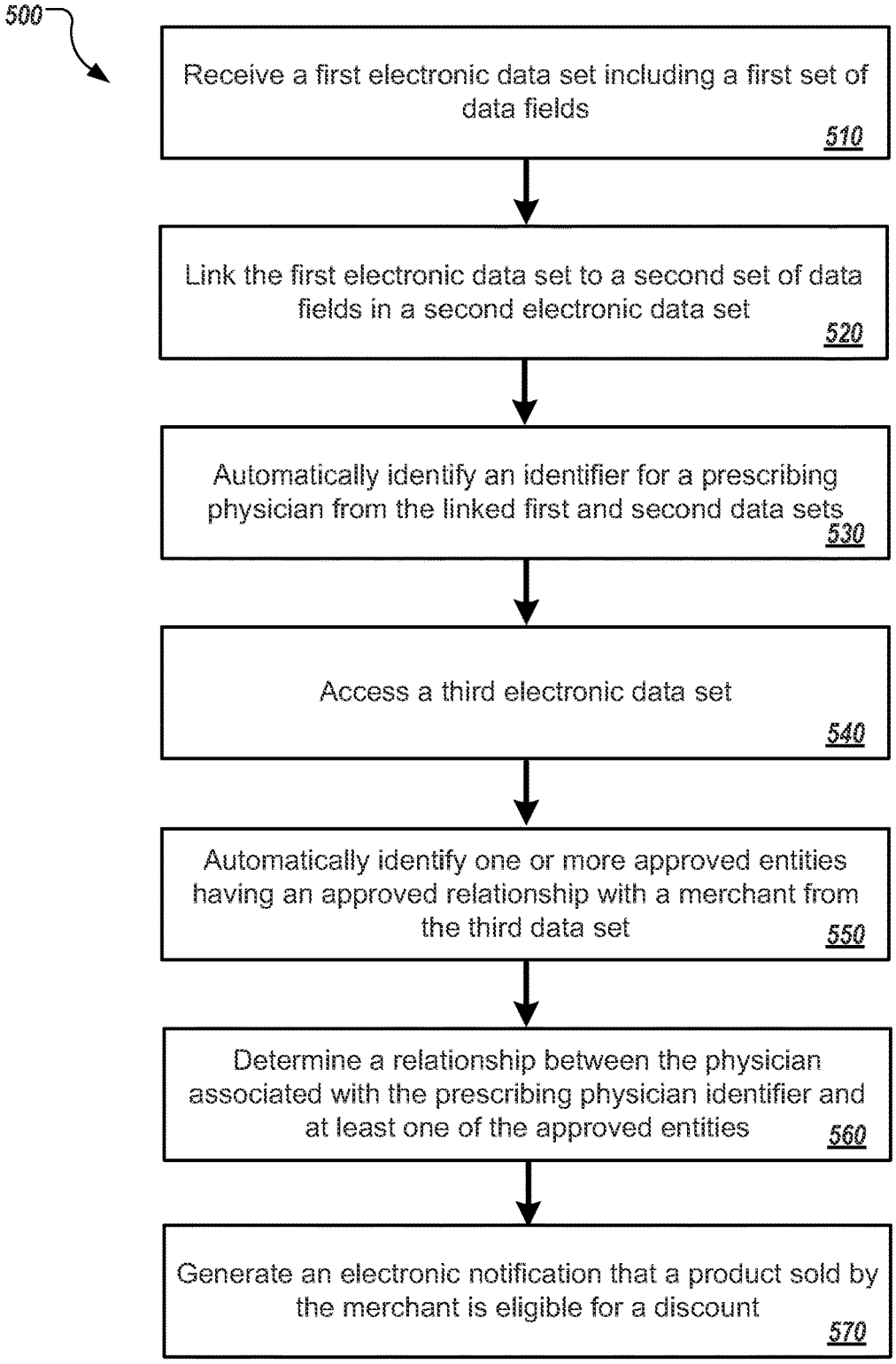
FIG. 5 depicts an example data reconciliation process that can be executed in accordance with implementations of the present disclosure.

FIG. 5 depicts an example data reconciliation process 500 that can be executed in accordance with implementations of the present disclosure. In some examples, the example process 500 can be provided as one or more computer-executable programs executed using one or more computing devices such as, for example, DRS 116.

A first electronic data set including a first set of data fields is received from a first party (510). The first electronic data set can include prescription fulfillment data. For example, the first data set may be data received from an insurance PBM. The first electronic data set is linked to a second set of data fields from a second electronic data set (520). The second electronic data set can include third-party prescription information, and the data sets can be linked based on matching data from at least one of the first set of data fields of the first electronic data set to data from at least one of a second set of data fields of the second electronic data set. For example, data such as prescription identification numbers, seller identification, product identification numbers, and dispense dates can be matched between the two data sets. An identifier for a prescribing physician is automatically identified based on the linked first and second electronic data sets (530). For example, linking the data from the first and second data sets can reveal an identifier of the prescribing physician from the second data set.

A third electronic data set is accessed (540). The third electronic data set can include discount eligibility information and identify entities approved to receive a discount. One or more approved entities having an approved relationship with a merchant are automatically identified from the third data set (550). For example, the third data set may be a government database of entities approved to receive a government mandated discount (e.g., a 340B discount). The merchant may be associated with the merchant identifier from the first data set and, the one or more certified entities may be identified using the merchant identifier. A relationship between the physician associated with the prescribing physician identifier and at least one of the approved certified entities is determined (560). The relationship may be determined based on comparing the prescribing physician identifier and identifiers of the one or more approved entities to a fourth set of data fields from a fourth electronic data set. In some examples, the number and type of relationships that the physician has with both certified and other entities may be determined. The physician's relationships may be used to determine a confidence level associated with the likelihood that particular products were prescribed in connection with the physician's relationship with a certified entity. In response to determining the relationship between the physician and the at least one of the approved entities, an electronic notification indicating that a product sold by the merchant is eligible for the discount is automatically generated (570). The electronic notification can be an e-mail, text message, etc. In some examples, the notification includes applicable data from one or more of the data sets to document the determination. For example, the electronic notification can include a report of discount eligibility data related to multiple products sold by the manufacturer.

Implementations of the subject matter and the operations described in this specification can be realized in digital electronic circuitry, or in computer software, firmware, or hardware, including the structures disclosed in this specification and their structural equivalents, or in combinations of one or more of them. Implementations of the subject matter described in this specification can be realized using one or more computer programs, i.e., one or more modules of computer program instructions, encoded on computer storage medium for execution by, or to control the operation of, data processing apparatus. Alternatively or in addition, the program instructions can be encoded on an artificially generated propagated signal, for example, a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer, storage medium is not a propagated signal; a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, for example, an FPGA (field programmable gate array) or an ASIC (application-specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, for example, an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer can include a processor for performing actions in accordance with instructions and one or more memory devices for storing instructions and data. Generally, a computer will also include, or be operatively coupled to receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, for example, EPROM, EEPROM, and flash memory devices; magnetic disks, for example, internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented on a computer having a display device, for example, a CRT (cathode ray tube) or LCD (liquid crystal display) monitor, for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this specification can be implemented in a computing system that includes a back-end component (e.g., such as a data server), or that includes a middleware component (e.g., an application server), or that includes a front-end component (e.g., a client computer having a graphical user interface or a Web browser through which a user can interact with an implementation of the subject matter described in this specification), or any combination of one or more such back-end, middleware, or front-end components. The components of the system can be interconnected by any form or medium of digital data communication (e.g., a communication network). Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any implementation of the present disclosure or of what may be claimed, but rather as descriptions of features specific to example implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method for reconciling data across electronic data sources with distinct feature sets, the method executed by one or more processors, and the method comprising:

receiving, by a data reconciliation system, a first data set including:

a first set of data fields, and electronic prescription fulfillment data, wherein the first set of data fields includes at least a merchant identifier for a merchant;

determining, by the data reconciliation system, a match between:

a first data datum from a data field of the first set of data fields, and a second datum from a data field of a second set of data fields, wherein:

the second set of data fields is included in a second data set, the second data set is distinct from the first data set, and the second data set includes third-party prescription information;

generating, by the data reconciliation system, a linked database comprising links between the first data set and the second set of data fields, the links based on the match between the first datum and the second datum;

identifying, by the data reconciliation system, a physician identifier for a physician that prescribed a product provided by the merchant, wherein the physician identifier is automatically identified by analyzing the linked database to obtain information from corresponding data fields of the first and second data sets;

identifying, by the data reconciliation system, one or more entities having an approved relationship with the merchant, based on the merchant identifier;

generating, by the data reconciliation system, a confidence score that characterizes a relationship between the physician and an entity by comparing the physician identifier and a respective identifier for each of the one or more entities, based on information in the linked database;

determining, by the data reconciliation system, a confidence level that indicates information in the linked database accurately identifies products that are eligible to be obtained for a predefined amount, wherein the confidence level is determined based on the confidence score exceeding a threshold confidence score and the relationship between the physician and the entity, and providing, by the data reconciliation system, an electronic notification that includes information indicating the product prescribed by the physician and provided by the merchant is eligible to be obtained for the predefined amount.

2. The method of claim 1, further comprising reconciling data from the first and second data sets with data from a plurality of other data sets to determine information related to a sale of the product, and wherein the electronic notification includes the information related to the sale of the product.

3. The method of claim 1, further comprising:

determining the relationship between the physician associated with the physician identifier and the entity existed on a dispense date of the product, the dispense date included in datum from the first set of data fields.

4. The method of claim 1, further comprising determining, from data in a third electronic data set, that the approved relationship between the merchant and the one or more entities with which the physician has a relationship existed on a dispense date of the product, the dispense date included in datum from the first set of data fields.

5. The method of claim 1, wherein the electronic notification includes the confidence score, the confidence score indicating a likelihood that the product is eligible to be obtained for the predefined amount.

6. The method of claim 5, wherein the confidence score is determined based on a type of the relationship between the physician and one or more entities.

7. The method of claim 5, wherein the confidence score is determined based on a number of relationships that the physician has with approved entities.

8. The method of claim 1, wherein the second data set is a secure data set, the method further comprising accessing the second data set from a secure data repository.

9. The method of claim 1, wherein the predefined amount is a government mandated transaction amount that is associated with a third data set that is a government maintained data set.

10. A system comprising:

one or more processors; and a data store coupled to the one or more processors having instructions stored thereon which, when executed by the one or more processors, causes the one or more processors to perform operations comprising:

receiving, by a data reconciliation system, a first data set including:

a first set of data fields, and electronic prescription fulfillment data, wherein the first set of data fields includes at least a merchant identifier for a merchant;

determining, by the data reconciliation system, a match between:

a first data datum from a data field of the first set of data fields, and a second datum from a data field of a second set of data fields, wherein:

the second set of data fields is included in a second data set, the second data set is distinct from the first data set, and the second data set includes third-party prescription information;

generating, by the data reconciliation system, a linked database comprising links between the first data set and the second set of data fields, the links based on the match between the first datum and the second datum;

identifying, by the data reconciliation system, a physician identifier for a physician that prescribed a product provided by the merchant, wherein the physician identifier is automatically identified by analyzing the linked database to obtain information from corresponding data fields of the first and second data sets;

identifying, by the data reconciliation system, one or more entities having an approved relationship with the merchant, based on the merchant identifier;

generating, by the data reconciliation system, a confidence score that characterizes a relationship between the physician and an entity by comparing the physician identifier and a respective identifier for each of the one or more entities, based on information in the linked database;

determining, by the data reconciliation system, a confidence level that indicates information in the linked database accurately identifies products that are eligible to be obtained for a predefined amount, wherein the confidence level is determined based on the confidence score exceeding a threshold confidence score and the relationship between the physician and the entity, and providing, by the data reconciliation system, an electronic notification that includes information indicating the product prescribed by the physician and provided by the merchant is eligible to be obtained for the predefined amount.

11. The system of claim 10, wherein the operations further comprise reconciling data from the first and second data sets with data from a plurality of other data sets to determine information related to a sale of the product, and wherein the electronic notification includes the information related to the sale of the product.

12. The system of claim 10, wherein the operations further comprise:

determining the relationship between the physician associated with the physician identifier and the entity existed on a dispense date of the product, the dispense date included in datum from the first set of data fields.

13. The system of claim 10, wherein the operations further comprises:

determining, from data in a third electronic data set, that the approved relationship between the merchant and the one or more entities with which the physician has a relationship merchant existed on a dispense date of the product, the dispense date included in datum from the first set of data fields.

14. The system of claim 10, wherein the electronic notification includes the confidence score, the confidence score indicating a likelihood that the product is eligible to be obtained for the predefined amount.

15. The system of claim 14, wherein the confidence score is determined based on a type of the relationship between the physician and one or more entities.

16. The system of claim 14, wherein the confidence score is determined based on a number of relationships that the physician has with approved entities.

17. The system of claim 10, wherein the second data set is a secure data set, the method further comprising accessing the second data set from a secure data repository.

18. A non-transient computer readable medium storing instructions that, when executed by one or more processors, cause the one or more processors to perform operations comprising:

receiving, by a data reconciliation system, a first data set including:

a first set of data fields, and electronic prescription fulfillment data, wherein the first set of data fields includes at least a merchant identifier for a merchant;

determining, by the data reconciliation system, a match between:

a first data datum from a data field of the first set of data fields, and a second datum from a data field of a second set of data fields, wherein, the second set of data fields is included in a second data set, the second data set is distinct from the first data set, and the second data set includes third-party prescription information;

generating, by the data reconciliation system, a linked database comprising links between the first data set and the second set of data fields, the links based on the match between the first datum and the second datum;

identifying, by the data reconciliation system, a physician identifier for a physician that prescribed a product provided by the merchant, wherein the physician identifier is automatically identified by analyzing the linked database to obtain information from corresponding data fields of the first and second data sets;

identifying, by the data reconciliation system, one or more entities having an approved relationship with the merchant, based on the merchant identifier;

generating, by the data reconciliation system, a confidence score that characterizes a relationship between the physician and an entity by comparing the physician identifier and a respective identifier for each of the one or more entities, based on information in the linked database;

determining, by the data reconciliation system, a confidence level that indicates information in the linked database accurately identifies products that are eligible to be obtained for a predefined amount, wherein the confidence level is determined based on the confidence score exceeding a threshold confidence score and the relationship between the physician and the entity, and providing, by the data reconciliation system, an electronic notification that includes information indicating the product prescribed by the physician and provided by the merchant is eligible to be obtained for the predefined amount.

19. The medium of claim 18, wherein the operations further comprise reconciling data from the first and second data sets with data from a plurality of other data sets to determine information related to a sale of the product, and wherein the electronic notification includes the information related to the sale of the product.

20. The medium of claim 18, wherein the operations further comprise:

determining the relationship between the physician associated with the physician identifier and entity existed on a dispense date of the product, the dispense date included in datum from the first set of data fields.

*21. A computer system-implemented method comprising:*

*determining, by one or more processors of the computer system, a relationship between (i) a first data record of a first data set, the first data record containing first data indicative of a prescription, the first data including a merchant identifier of a merchant, and (ii) a second data record of a second data set, the second data record containing second data indicative of the prescription, including matching data from a data field of the first data record set to data from a data field of the second data record;*

*analyzing, by the one or more processors, the first data record and the second data record to identify a physician identifier for a physician associated with the prescription;*

*identifying, by the one or more processors and based on the merchant identifier contained in the first data record and the physician identifier, an entity having an relationship with both the merchant and the physician;*

*generating, by the one or more processors, a confidence score characterizing the relationship between the entity and the physician by comparing the physician identifier and an identifier for the entity;*

*determining, by the one or more processors, a confidence level indicating that information in the first data set and second data set accurately identify products that are eligible for a predefined amount, including determining the confidence level based on the confidence score exceeding a threshold and based on the relationship between the physician and the entity; and*

*generating, by the one or more processors, an electronic notification indicating that a product prescribed by the physician and provided by the merchant is eligible to be obtained for the predefined amount.*

*22. The computer system-implemented method of claim 21, comprising storing, in a database of the computer*

*system, data indicative of the relationship between the first data record and the second data record.*

*23. The computer system-implemented method of claim 22, comprising generating a link, in the database, between the first data record and the second data record.*

*24. The computer system-implemented method of claim 21, in which identifying an entity having a relationship with both the merchant and the physician comprises accessing a third data set containing third data indicative of information about eligibility for the predefined amount and entities eligible to obtain products for the predefined amount.*

*25. The computer system-implemented method of claim 24, comprising reconciling data records of the first data set and data records of the second data set with data records of the third data set.*

*26. The computer system-implemented method of claim 21, comprising determining the confidence score based on a number of relationships that the physician has with entities.*

*27. The computer system-implemented method of claim 21, comprising determining the confidence score based on a type of the relationship between the physician and each of one or more entities.*

*28. The computer system-implemented method of claim 21, comprising accessing the second data set from a secure data repository.*

*29. A non-transitory computer readable medium storing instructions to cause a computer system to:*

*determine, by one or more processors of the computer system, a relationship between (i) a first data record of a first data set, the first data record containing first data indicative of a prescription, the first data including a merchant identifier of a merchant, and (ii) a second data record of a second data set, the second data record containing second data indicative of the prescription, including matching data from a data field of the first data record set to data from a data field of the second data record;*

*analyze, by the one or more processors, the first data record and the second data record to identify a physician identifier for a physician associated with the prescription;*

*identify, by the one or more processors and based on the merchant identifier contained in the first data record and the physician identifier, an entity having an relationship with both the merchant and the physician;*

*generate, by the one or more processors, a confidence score characterizing the relationship between the entity and the physician by comparing the physician identifier and an identifier for the entity;*

*determine, by the one or more processors, a confidence level indicating that information in the first data set and second data set accurately identify products that are eligible for a predefined amount, including determining the confidence level based on the confidence score exceeding a threshold and based on the relationship between the physician and the entity; and*

*generate, by the one or more processors, an electronic notification indicating that a product prescribed by the physician and provided by the merchant is eligible to be obtained for the predefined amount.*

*30. The non-transitory computer readable medium of claim 29, in which the instructions cause the computer system to store, in a database of the computer system, data indicative of the relationship between the first data record and the second data record.*

*31. The non-transitory computer readable medium of claim 30, in which the instructions cause the computer system to generate a link, in the database, between the first data record and the second data record.*

*32. The non-transitory computer readable medium of claim 29, in which identifying an entity having a relationship with both the merchant and the physician comprises accessing a third data set containing third data indicative of information about eligibility for the predefined amount and entities eligible to obtain products for the predefined amount.*

*33. The non-transitory computer readable medium of claim 32, in which the instructions cause the computer system to reconcile data records of the first data set and data records of the second data set with data records of the third data set.*

*34. The non-transitory computer readable medium of claim 29, in which the instructions cause the computer system to determine the confidence score based on a number of relationships that the physician has with entities.*

*35. The non-transitory computer readable medium of claim 29, in which the instructions cause the computer system to determine the confidence score based on a type of the relationship between the physician and each of one or more entities.*

*36. The non-transitory computer readable medium of claim 29, in which the instructions cause the computer system to access the second data set from a secure data repository.*

*37. A computer system comprising:*

*one or more processors coupled to a memory, the one or more processors and memory configured to:*

*determine, by the one or more processors, a relationship between (i) a first data record of a first data set, the first data record containing first data indicative of a prescription, the first data including a merchant identifier of a merchant, and (ii) a second data record of a second data set, the second data record containing second data indicative of the prescription, including matching data from a data field of the first data record set to data from a data field of the second data record;*

*analyze, by the one or more processors, the first data record and the second data record to identify a physician identifier for a physician associated with the prescription;*

*identify, by the one or more processors and based on the merchant identifier contained in the first data record and the physician identifier, an entity having an relationship with both the merchant and the physician;*

*generate, by the one or more processors, a confidence score characterizing the relationship between the entity and the physician by comparing the physician identifier and an identifier for the entity;*

*determine, by the one or more processors, a confidence level indicating that information in the first data set and second data set accurately identify products that are eligible for a predefined amount, including determining the confidence level based on the confidence score exceeding a threshold and based on the relationship between the physician and the entity; and*

*generate, by the one or more processors, an electronic notification indicating that a product prescribed by the physician and provided by the merchant is eligible to be obtained for the predefined amount.*

*38. The computer system of claim 37, in which the one or more processors and memory are configured to store, in a*

*database of the computer system, data indicative of the relationship between the first data record and the second data record.*

*39. The computer system of claim 38, in which the one or more processors and memory are configured to generate a link, in the database, between the first data record and the second data record.*

*40. The computer system of claim 37, in which identifying an entity having a relationship with both the merchant and the physician comprises accessing a third data set containing third data indicative of information about eligibility for the predefined amount and entities eligible to obtain products for the predefined amount.*

*41. The computer system of claim 40, in which the one or more processors and memory are configured to reconcile data records of the first data set and data records of the second data set with data records of the third data set.*

*42. The computer system of claim 37, in which the one or more processors and memory are configured to determine the confidence score based on a number of relationships that the physician has with entities.*

*43. The computer system of claim 37, in which the one or more processors and memory are configured to determine the confidence score based on a type of the relationship between the physician and each of one or more entities.*

*44. The computer system of claim 37, in which the one or more processors and memory are configured to access the second data set from a secure data repository.*

* * * * *